(12) United States Patent
Dan et al.

(10) Patent No.: US 11,382,914 B2
(45) Date of Patent: *Jul. 12, 2022

(54) USAGE AND DOSAGE OF THERAPEUTIC AGENTS FOR ENDOMETRIOSIS

(71) Applicant: KISSEI PHARMACEUTICAL CO., LTD., Matsumoto (JP)

(72) Inventors: Takuro Dan, Tokyo (JP); Hideomi Takahashi, Tokyo (JP); Yu Kuramochi, Tokyo (JP)

(73) Assignee: KISSEI PHARMACEUTICAL CO., LTD., Nagano (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,260

(22) Filed: Apr. 8, 2020

(65) Prior Publication Data

US 2021/0046078 A1    Feb. 18, 2021

Related U.S. Application Data

(63) Continuation of application No. 16/322,227, filed as application No. PCT/JP2017/028504 on Aug. 7, 2017, now Pat. No. 10,646,491.

(30) Foreign Application Priority Data

Aug. 8, 2016   (JP) ................................. 2016-155175

(51) Int. Cl.
| | | |
|---|---|---|
| A61K 31/519 | (2006.01) | |
| A61P 15/00 | (2006.01) | |
| A61P 29/00 | (2006.01) | |
| A61P 15/02 | (2006.01) | |

(52) U.S. Cl.
CPC ............ *A61K 31/519* (2013.01); *A61P 15/00* (2018.01); *A61P 29/00* (2018.01)

(58) Field of Classification Search
CPC ........ A61K 31/519; A61P 15/00; A61P 29/00; A61P 15/02
See application file for complete search history.

(56) References Cited

U.S. PATENT DOCUMENTS

| | | | |
|---|---|---|---|
| 9,040,693 B2 | 5/2015 | Ohno et al. | |
| 2009/0325900 A1 | 12/2009 | Ohno et al. | |
| 2013/0059867 A1 | 3/2013 | Jo et al. | |

FOREIGN PATENT DOCUMENTS

| | | |
|---|---|---|
| WO | 2007/046392 A1 | 4/2007 |
| WO | 2011/099507 A1 | 8/2011 |

OTHER PUBLICATIONS

Diamond, M.P.. "Elagolix treatment for endometriosis-associated pain: results from a phase 2, randomized, double-blind, placebo-controlled study." Reproductive sciences 21.3 (2014): 363-371.*

Osuga, Y., "Physiology and Pathology of GnRH and Clinical Applications of GnRH: GnRH Analogues and Clinical Applications of GnRH Antagonists Endometriosis", Japanese Journal of Clinical Medicine, 2006, vol. 64, Suppl 4, pp. 112-115 (w/ English translation; cited in the ISR).

Kupker W., et al., "Use of GnRH antagonists in the treatment of endometriosis", Reproductive BioMedicine Online (www.rbmonline.com/Article/442), May 2002, vol. 5, No. 1, pp. 12-16 (in English; cited in the ISR).

Barbieri, "Endometriosis and the Estrogen Threshold Theory", The Journal of Reproductive Medicine, vol. 43, No. 3, Mar. 1998, pp. 287-292 (in English; cited in the Specification).

International Search Report dated Sep. 26, 2017 issued in counterpart International Application No. PCT/JP2017/028504 (2 pages, in English).

Extended European Search Report, dated Feb. 19, 2020, issued in counterpart European Application No. 17839388.0 (in English; 4 pages).

Ezzati, M. et al., "Elagolix, a novel, orally bioavailable GnRH antagonist under investigation for the treatment of endometriosis-related pain", Women's Health, Future Medicine, UK, vol. 11, No. 1, pp. 19-28 (Jan. 1, 2015) (in English; cited in EESR).

MacKay, K., "ObsEva SA", retrieved from internet at URL: http://research-doc.credit-suisse.com/docView?language=ENG&format=PDF&sourceid=csplusresearchcp&document_id=1071589801&serialid=w%tUz5ckZojLgop%2BFQZCZvq2JSqlpv%2FqYEO7ASCs3s0%3D, pp. 1-44 (Feb. 21, 2017) (in English; cited in EESR).

Melis, G., et al., "Overview of elagolix for the treatment of endometriosis", Expert Opinion on Drug Metabolism & Toxicology, vol. 12, No. 5, 2016, pp. 581-588 (in English, U.S. Appl. No. 16/322,227).

* cited by examiner

*Primary Examiner* — John M Mauro
(74) *Attorney, Agent, or Firm* — WHDA, LLP

(57) ABSTRACT

An object of the present invention is to provide pharmaceutical agents that reduce risk for decrease in bone mineral density due to their effect of reducing estrogen levels and exert excellent therapeutic effects on endometriosis. The present invention relates to pharmaceutical compositions for treating endometriosis comprising 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid or a pharmaceutically acceptable salt thereof, which are administered orally once a day at a daily dose of between 50 mg and 75 mg calculated as a free form.

20 Claims, 2 Drawing Sheets

USAGE AND DOSAGE OF THERAPEUTIC AGENTS FOR ENDOMETRIOSIS

CROSS-REFERENCE TO RELATED APPLICATIONS

This application is a continuation of U.S. application Ser. No. 16/322,227, filed on Jan. 31, 2019, which is a U.S. National Stage entry of International Application No. PCT/JP2017/028504 filed on Aug. 7, 2017, which claims priority from Japanese Patent Application No. 2016-155175 filed on Aug. 8, 2016, the entire disclosure of each of the foregoing is herein incorporated by reference.

TECHNICAL FIELD

The present invention relates to pharmaceutical agents that reduce risk for decrease in bone mineral density due to their effect of reducing estrogen levels and exert their excellent therapeutic effects on endometriosis.

More specifically, the present invention relates to pharmaceutical compositions for treating endometriosis comprising 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid or a pharmaceutically acceptable salt thereof, which are administered orally once a day at a daily dose of between 50 mg and 75 mg calculated as a free form.

BACKGROUND ART

Endometriosis is a disease in which endometrium or similar tissue grows at sites outside the uterus depending on the increased estrogen level. Although endometriosis is a benign disease, it causes pain such as menstrual pain and reduces fertility, and significantly reduces the quality of life (QOL) of women in their social and reproductive activities. Women with endometriosis have menstrual pain at an extremely high frequency and a symptom of pain such as lower abdominal pain not at their menstruation, low back pain, pain during or after sexual intercourse, pain during defecation and so on at a high frequency.

Many patients repeat exacerbation or recurrence of endometriosis before the menopause and thus endometriosis requires long-term treatment and management, unless they receive a radical surgical operation. As the first treatment for endometriosis, medication therapy is often selected. Medication therapy is generally classified into symptomatic and endocrine therapies. For symptomatic therapy, a medicine such as an analgesic agent is used in order to reduce endometriosis-associated pain. For endocrine therapy, in addition to reduction of pain, a low-dose formulated estrogen-progestin agent, dienogest, or gonadotropin releasing hormone (GnRH) agonist is used in order to suppress estrogen-dependent growth of endometrium.

Analgesic agents, however, have been considered not to be able to reduce endometriosis-associated pain in 10% to 30% of patients with endometriosis. Furthermore, in using a low-dose formulated estrogen-progestin agent, care should be taken for thrombosis, liver dysfunction and the others. Dienogest has been reported in a long-term study to have a 71.9% incidence of atypical genital bleeding as a side effect, which may result in severe anemia. GnRH agonists are, basically, not allowed to be administered for more than 6 months for a possible decrease of bone mineral density due to a decline in estrogen levels.

As described above, in medication therapy for treating endometriosis, continuous administration of medicament is difficult in many patients due to side effects specific for each of pharmaceutical agents. Accordingly, development of pharmaceutical agents that have fewer side effects and can be administered for a long period has been desired.

In the treatment of endometriosis, a concept called "estradiol therapeutic window" has been proposed as a threshold for blood estradiol (E2) level under which serious decrease of bone mineral density due to the effect of reducing estrogen levels does not occur while suppressing growth of the lesions of endometriosis (NPL 1). For example, NPL 1 describes that a therapeutic window would be an E2 level between 30 pg/mL and 50 pg/mL. Furthermore, it suggests that, at estradiol concentrations of lower than 20 pg/ml, the legions of endometriosis should atrophy but decrease of bone mineral density should be prominent.

3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid (hereinafter, referred to as Compound 1) represented by the following formula (I) is described in PTL 1. A choline salt of Compound 1 (hereinafter, referred to as Compound 2) is described in PTL 2. PTL 1 and PTL 2 describe that the Compound 2 and fused heterocyclic derivatives containing Compound 1 antagonize GnRH and can be used as pharmaceutical agents for preventing or treating sex hormone-dependent diseases such as prostatic hypertrophy, uterine fibrosis, endometriosis, uterine fibroma, precocious puberty, amenorrhea, premenstrual syndrome, and dysmenorrhea. PTL 1 and PTL 2 also describe that an oral dosage form can be manufactured in such a manner that the fused heterocyclic derivative or Compound 2 is administered at a dose ranging between 0.1 mg and 1000 mg.

[Chemical Formula 1]

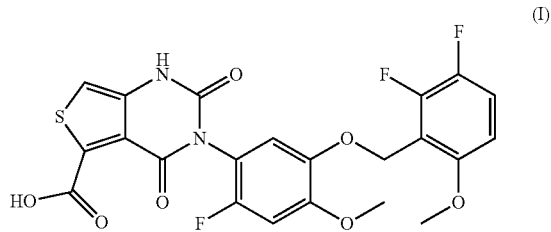

(I)

PTL 1 and PTL 2 only describe general medical applications and general dosage of Compound 2 and fused heterocyclic derivatives containing Compound 1 based on GnRH antagonist activity. They do not specifically describe usages and dosages of Compounds 1 and 2 with which risk for decrease in bone mineral density due to their effect of reducing estrogen levels is reduced and their excellent therapeutic effects are exerted on endometriosis.

CITATION LIST

Patent Literature

PTL 1: International Publication WO2007/046392
PTL 2: International Publication WO2011/099507

Non Patent Literature

NPL 1: Robert L. Barbieri, "The Journal of Reproductive Medicine," 1998, 43, supplement, 287-292

SUMMARY OF INVENTION

Problems to be Solved by the Invention

An object of the present invention is to provide pharmaceutical agents that reduce risk for decrease in bone mineral density due to their effect of reducing estrogen levels and exert excellent therapeutic effects on endometriosis.

Means for Solving the Problems

The present inventors found, as a result of extensive studies to achieve the aforementioned object, an optimum balance of efficacy and side effects as well as usages and dosages of Compound 1 with which risk for decrease in bone mineral density due to its effect of reducing estrogen levels is reduced.

The present invention relates to the following [1] to [5].
[1] A pharmaceutical composition for treating endometriosis comprising 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid or a pharmaceutically acceptable salt thereof, the compound being administered orally once a day at a daily dose of between 50 mg and 75 mg calculated as a free form.
[2] The pharmaceutical composition according to [1], wherein the pharmaceutically acceptable salt is 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid choline salt.
[3] The pharmaceutical composition according to [1] or [2], wherein the daily dose is 50 mg calculated as a free form.
[4] The pharmaceutical composition according to [1] or [2], wherein the daily dose is 75 mg calculated as a free form.
[5] The pharmaceutical composition according to any one of [1] to [4], wherein the composition for treating endometriosis is a composition for treating endometriosis-associated pain.

As one embodiment, the present invention relates to a method of treating endometriosis comprising administering a necessary amount of a pharmaceutical composition containing 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid or a pharmaceutically acceptable salt thereof to a patient, wherein the compound is administered orally once a day at a daily dose of between 50 mg and 75 mg calculated as a free form.

As one embodiment, the present invention relates to use of 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid or a pharmaceutically acceptable salt thereof for manufacturing a pharmaceutical composition for treating endometriosis, wherein the compound is administered orally once a day at a daily dose of between 50 mg and 75 mg calculated as a free form.

Advantageous Effects of Invention

The pharmaceutical compositions of the present invention reduce risk for decrease in bone mineral density due to their effects of decline in estrogen levels and exert their excellent therapeutic effects on endometriosis.

MODE FOR CARRYING OUT THE INVENTION

Figure 1:
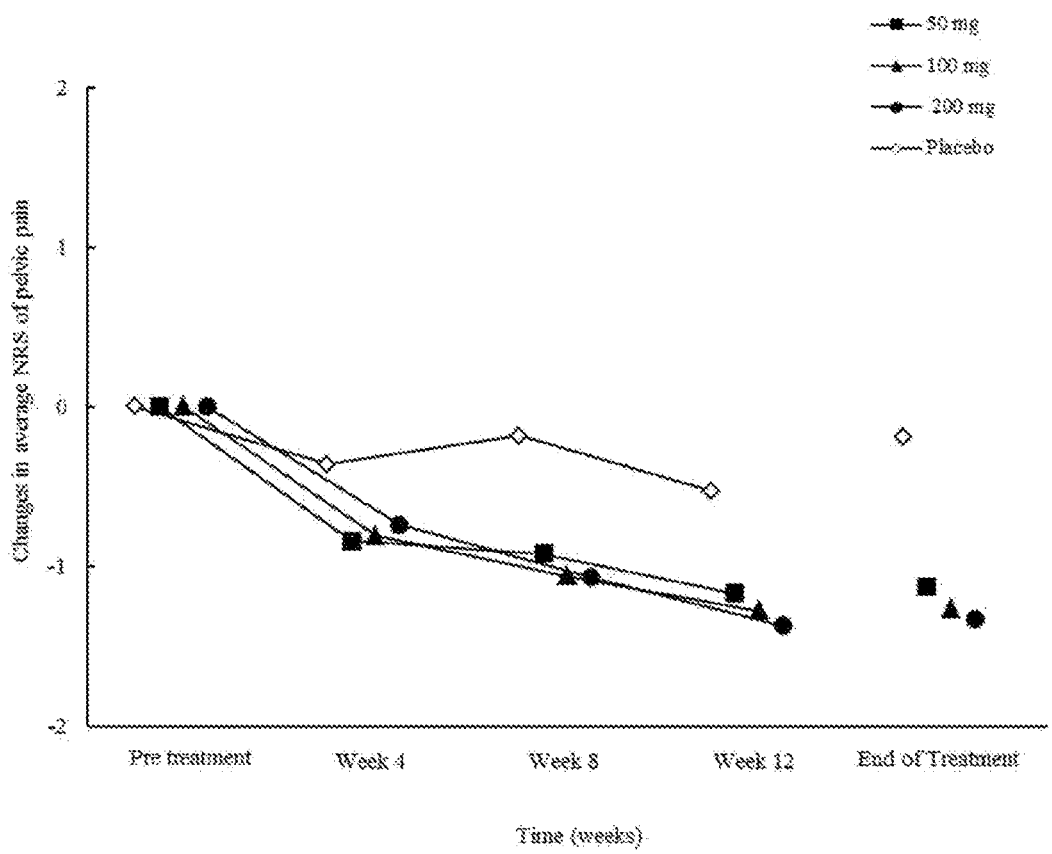
FIG. 1 shows NRS scores of patients with endometriosis. The vertical axis represents changes in average NRS for pelvic pain (regardless of whether subjects were at their menstruation or not) from the pre-treatment period (Changes in average NRS of pelvic pain). The horizontal axis represents time of measurements. "Pre treatment" represents the pre-treatment period, "Week 4," "Week 8," and "Week 12" represent 4 weeks, 8 weeks, and 12 weeks, respectively, after the beginning of administration, and "End of Treatment" represents the time of final assessment during the treatment period. In the figure, black squares represent values for a group administered with 50 mg, black triangles represent values for a group administered with 100 mg, black circles represent values for a group administered with 200 mg, and white squares represent values for a placebo group.

Embodiments of the present invention are described more in detail below.

In the present invention, words and terms have the following meaning, unless specified otherwise.

In the present invention, Compound 1 means "3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid" and Compound 2 means "3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid choline salt." The Compound 1 and "5-carboxy-3-[2-fluoro-5-(2,3-difluoro-6-methoxybenzyloxy)-4-methoxyphenyl]thieno[3,4-d]pyrimidine-2,4 (1H,3H)-dione" described in PTL 1 are the same compound.

In the present invention, Compound 1 can be converted to a pharmaceutically acceptable salt thereof according to a general method, if necessary. Examples of such salts include sodium salts, potassium salts, and organic base salts such as N,N'-dibenzyl entylenediamine, 2-aminoethanol, and choline. A choline salt of Compound 1 (i.e., Compound 2) is preferable.

In the present invention, the term "pharmaceutically acceptable salt of Compound 1" also includes a solvate thereof with a pharmaceutically acceptable solvent such as water and ethanol.

Compounds 1 and 2 of the present invention can be produced using a known method. For example, Compounds 1 and 2 of the present invention can be manufactured using a method described in WO 2007/046392 (PTL 1) and WO 2011/099507 (PTL 2), respectively, or other similar method.

The pharmaceutical compositions of the present invention can take any one of various dosage forms depending on their usage. Examples of such dosage forms include oral formulations such as powders, granules, fine granules, dry syrups, tablets, and capsules.

The pharmaceutical compositions of the present invention are prepared using Compound 1 or a pharmaceutically acceptable salt thereof as an active ingredient, and at least one pharmaceutical additive. The pharmaceutical compositions of the present invention can also be prepared by being appropriately mixed with, diluted with or dissolved in a pharmaceutical additive using a pharmaceutically known method depending on their dosage form. Examples of such pharmaceutical additives include excipients such as lactose, lubricants such as magnesium stearate, disintegrating agents such as carboxymethyl cellulose, binders such as hydroxypropyl methylcellulose, surfactants such as macrogols, foaming agents such as sodium hydrogen carbonate, solubilizing agents such as cyclodextrin, acidifiers such as citric acid, stabilizers such as disodium edetate, and pH adjusting agents such as phosphates.

The pharmaceutical compositions of the present invention are useful as therapeutic agents for endometriosis and have one or more of effects of reducing pain (e.g., pelvic pain, pain during defecation, pain during vaginal examination, and pain during or after sexual intercourse) associated with endometriosis, effects of reducing the size of ovarian chocolate cysts associated with endometriosis, effects of improving objective findings (e.g., induration of Douglas' pouch and limited uterine mobility), and reduction in use rate for analgesic agents.

As one embodiment, since menstruation cycles are maintained during treatment of endometriosis depending on their embodiment, the pharmaceutical compositions of the present invention can be used for patients with endometrium who don't want to interrupt menstruation.

In the present invention, a daily dose of an active ingredient (Compound 1 or a pharmaceutically acceptable salt thereof) to adult patients can be determined within a range of between 50 mg and 75 mg for oral administration (if Compound 1 is in the form of a pharmaceutically acceptable salt thereof, it can be determined within a range of between 50 mg and 75 mg calculated as a free form). For example, for adult patients, an initial dosage can be 50 mg or 75 mg calculated as a free form of Compound 2, and Compound 2 can be administered orally at 50 mg or 75 mg calculated as a free from during treatment. The amount of Compound 2 used can appropriately be increased or decreased within a range between 25 mg and 100 mg calculated as a free form at the discretion of the physician depending on the age and body weight of the patient, extent of disease and/or level of side effects observed.

The pharmaceutical compositions of the present invention can be administered, for example, starting from the first to fifth days of menstruation.

Exemplified usage and dosage of the pharmaceutical compositions of the present invention can be as follows: Compound 2 is administered orally once a day at a daily dose of 50 mg or 75 mg calculated as a free form.

The daily dose can be increased or decreased within the aforementioned range at the discretion of the physician. The daily dose can be divided into two or three doses.

In the present invention, the phrase "risk for decrease in bone mineral density due to the effect of reducing estrogen levels" means risk for decrease in bone mineral density associated with suppression of E2 secretion. The degree of the "risk for decreased bone mineral density due to a decline in estrogen levels" by the pharmaceutical compositions of the present invention can be evaluated based on the E2 concentration or the development of symptoms of hypoestrogenism such as hot flashes, headache, dizziness and hyperhidrosis.

With the pharmaceutical compositions of the present invention, E2 can be adjusted to an appropriate concentration at which risk for decrease in bone mineral density due to the effect of reducing estrogen levels can be reduced. An appropriate E2 concentration is preferably between 20 pg/mL and 50 pg/mL, more preferably, between 30 pg/mL and 50 pg/mL during treatment.

The pharmaceutical compositions of the present invention can reduce side effects resulting from excessive suppression of E2 secretion, for example, the development of symptoms of hypoestrogenism such as hot flashes, headache, dizziness and hyperhidrosis associated with the administration of a pharmaceutical agent.

EXAMPLES

The present invention is further illustrated in more detail by way of the following Examples. However, the present invention is not limited thereto. In the Examples, the dosage (dose) of Compound 2 means a dosage calculated as a free form (value calculated as a free from) unless otherwise specified.

Example 1

Clinical Trial 1 in Patients with Endometriosis (Double-Blind Parallel-Group Comparison Study)
1. Methods To 107 patients with endometriosis, Compound 2 at a dose of 50 mg (29 patients), 100 mg (26 patients) or 200 mg (28 patients) or a placebo (24 patients) was orally administered after breakfast once a day for 12 weeks. These groups are hereinafter referred to as a 50-mg administration group, a 100-mg administration group, a 200-mg administration group, and a placebo group. The administration was started from the second to fifth days of menstruation.
2. Evaluation Scales for Effectiveness and Safety As evaluation scales for effectiveness, evaluated were, for example, NRS scores for pelvic pain at menstruation or at other time (from 0: no pain to 10: the strongest pain that the subject had experienced before), severity of pelvic pain at menstruation or at other time (from 0: no pain to 4: intolerable even after the use of an analgesic agent), temporary pain (pain during defecation, pain during vaginal examination, and pain during or after sexual intercourse), severity of observations by others (induration of Douglas' pouch and limited uterine mobility), use rate of an analgesic agent, sizes of an ovarian chocolate cyst and the uterus, endocrinological examinations (E2, luteinizing hormone (LH), follicle-stimulating hormone (FSH), and progesterone), and the presence or absence of menstruation.

As evaluation scales for safety, for example, the occurrence of an adverse event, the occurrence of a side effect, and vaginal bleeding were evaluated.
3. Results Changes of average NRS scores for pelvic pain (regardless of whether the subjects were at their menstruation or not) is shown in FIG. 1. Changes in average NRS for pelvic pain (regardless of whether the subjects were at their menstruation or not) between the pre-treatment period and the time of the final assessment during treatment were −1.13, −1.27, −1.33, and −0.19 for the 50-mg administration group, the 100-mg administration group, the 200-mg administration group, and the placebo group, respectively. Significant improvements were observed in all groups to which Compound 2 had been administered as compared to the placebo group. Temporal pain, observations by others, a use rate of an analgesic agent, sizes of an ovarian chocolate cyst and the uterus were also improved in the groups to which Compound 2 had been administered as compared to the placebo group.

The numbers of cases where side effects associated with hypoestrogenism (e.g., hot flashes, headache, dizziness and hyperhidrosis) were developed were 9, 12, 28, and 1 for the 50-mg administration group, the 100-mg administration group, the 200-mg administration group, and the placebo group, respectively.

Figure 2:
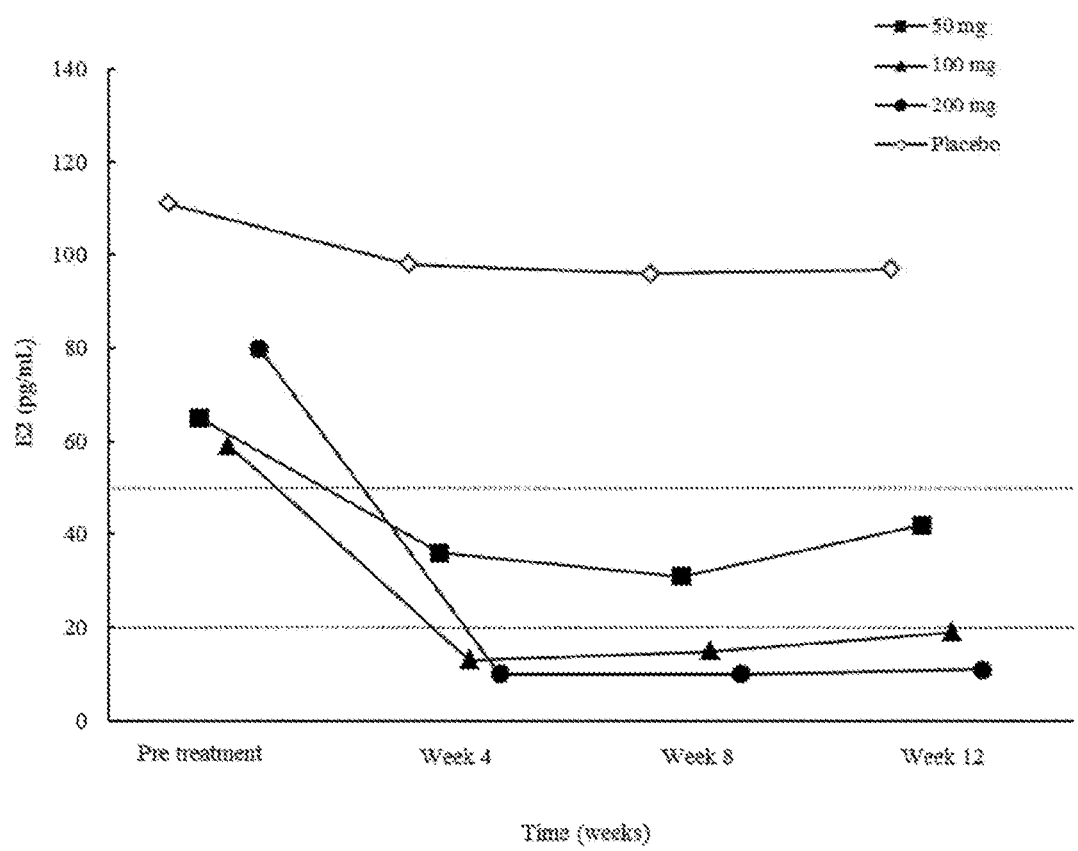
FIG. 2 shows E2 concentrations in patients with endometriosis during the treatment period. The vertical axis represents mean values of E2 concentrations (pg/m L). The horizontal axis represents time of measurements. "Pre treatment" represents the pre-treatment period, and "Week 4," "Week 8," and "Week 12" represent 4 weeks, 8 weeks, and 12 weeks, respectively, after the beginning of administration. In the figure, black squares represent values for a group administered with 50 mg, black triangles represent values for a group administered with 100 mg, black circles represent values for a group administered with 200 mg, and white squares represent values for a placebo group.

Changes of median E2 concentrations during treatment are shown in FIG. 2. Suppression of E2 secretion was observed in all groups to which Compound 2 had been administered. Analyses of the occurrences of side effects associated with hypoestrogenism (e.g., hot flashes, headache, dizziness and hyperhidrosis) for each E2 concentration during treatment revealed that the occurrence of side effects was 28.2% in the groups with E2 concentration of 20 pg/mL and/or more whereas the occurrence of side effects was 54.8% in the groups with E2 concentration of less than 20 pg/mL.

Table 1 shows whether menstruation occurred during treatment. In the table, "Compound 2 50 mg" means the 50-mg administration group, "Compound 2 100 mg" means the 100-mg administration group, "Compound 2 200 mg" means the 200-mg administration group, "Placebo" means the placebo group, "Yes" represents a percentage of patients who had menstruation during treatment, and "No" represents a percentage of patients who had no menstruation during treatment. When it was administered at a smaller dose, a higher percentage of patients had menstruation during treatment.

TABLE 1

|  | Yes | No |
| --- | --- | --- |
| Compound 2 50 mg | 72.4% | 27.6% |
| Compound 2 100 mg | 26.9% | 73.1% |
| Compound 2 200 mg | 3.6% | 96.4% |
| Placebo | 100.0% | 0.0% |

Results of Example 1 showed that, in the 50-mg administration group, a therapeutic effect on endometriosis-associated pain was similar to those in the 100-mg and 200-mg administration groups, and risk for decrease in bone mineral density due to the effect of reducing estrogen levels can be reduced.

On the other hand, in the 100-mg and 200-mg administration groups, sufficient therapeutic effects on endometriosis-associated pain were shown but side effects of symptoms of hypoestrogenism appeared at a higher frequency, and E2 concentrations during treatment were lower than 20 pg/mL.

It was also shown that side effects of symptoms of hypoestrogenism were reduced in the groups with E2 concentration of 20 pg/mL and/or more during treatment as compared to the groups with E2 concentration of less than 20 pg/mL.

Example 2

Clinical Trial 2 in Patients with Endometriosis (Randomized Non Blind Parallel-Group Comparison Study)
1. Methods To 21 patients with endometriosis, Compound 2 was administered orally at a dose of 75 mg (11 patients) or 150 mg (10 patients) after breakfast once a day for 8 weeks. These groups are hereinafter referred to as a 75-mg administration group and a 150-mg administration group. The administration was started from the second to fifth days of menstruation.

2. Evaluation Scales for Effectiveness and Safety

Scales similar to those in the Example 1 were evaluated as evaluation scales for effectiveness and safety.
3. Results Changes in average NRS for pelvic pain (regardless of whether the subjects were at their menstruation or not) between the pre-treatment period and the time of final assessment during the treatment period were −0.94 and −1.68 for the 75-mg administration group and the 150-mg administration group, respectively. A tendency of improvement was observed in all groups to which Compound 2 had been administered.

Median E2 concentrations during treatment were 35 pg/mL and 10 pg/mL on week 4 and 24 pg/mL and 10 pg/mL on week 8 for the 75-mg and 150-mg administration groups, respectively.

Results of the Example 2 showed that, in the 75-mg administration group also, a therapeutic effect was exhibited close to those obtained in the 100-mg and 200-mg administration groups on endometriosis-associated pain, and risk for decrease in bone mineral density due to the effect of reducing estrogen levels can be reduced.

Example 3

Clinical Trial 3 in Patients with Endometriosis (Randomized Double-Blind Parallel-Group Comparison Study)
1. Methods To a recruiting goal of 400 patients with endometriosis, Compound 2 is orally administered at a dose of 25 mg, 50 mg, 75 mg or 100 mg or a placebo after breakfast once a day for 12 weeks. The administration is started from the first to fifth days of menstruation.
2. Evaluation Scales for Effectiveness and Safety As evaluation scales for effectiveness, evaluated are, for example, NRS scores for pelvic pain at menstruation or at other time (from 0: no pain to 10: strongest pain that the subject have had before), severity of pelvic pain at menstruation or at other time (from 0: no pain to 4: intolerable even after the use of an analgesic agent), temporary pain (pain during defecation, pain during vaginal examination, and pain during or after sexual intercourse), severity of observations by others (induration of Douglas' pouch and limited uterine mobility), sizes of an ovarian chocolate cyst and the uterus, QOL (Endometriosis Health Profile-30 (EHP-30)), a use rate of an analgesic agent, endocrinological examinations (E2, luteinizing hormone (LH), follicle-stimulating hormone (FSH), and progesterone), and the presence or absence of menstruation.

As evaluation scales for safety, evaluated are, for example, the occurrence of an adverse event, the occurrence of a side effect, vaginal bleeding, bone metabolism markers (serum cross-linked N-telopeptide of type I collagen (serum NTX) and bone alkaline phosphatase (BAP)) and bone density (using the DXA method).

Results of the Examples 1 and 2 indicated that oral administration of Compound 2 at a daily dose of between 50 mg and 75 mg calculated as a free form once a day resulted in reduced risk for decrease in bone mineral density due to the effect of reducing estrogen levels and exerted excellent therapeutic effects on endometriosis.

INDUSTRIAL APPLICABILITY

The pharmaceutical compositions of the present invention are extremely useful as therapeutic agents for endometriosis.

The invention claimed is:

1. A method of reducing menstrual pain due to endometriosis in a human patient in need thereof, the method comprising administering to the patient a compound represented by 3-[2-fluoro-5-(2,3-difluoro-6-methoxybenzyloxy)-4methoxyphenyl]-2,4-dioxo-1,2,3,4-tetrahydrothieno[3,4-d]pyrimidine-5-carboxylic acid, or a pharmaceutically acceptable salt thereof, wherein the compound is administered to the patient in an amount of 75 mg, calculated as a free form, per day.

2. The method of claim 1, wherein the compound is administered to the patient in the form of a pharmaceutically acceptable salt thereof.

3. The method of claim 2, wherein the pharmaceutically acceptable salt is 3-[2-fluoro-5-(2,3-difluoro-6methoxybenzyloxy)-4-methoxyphenyl]-2,4-dioxo-1,2,3,4-tetrahydrothieno[3,4-d]pyrimidine-5carboxylic acid choline salt.

4. The method of claim 1, wherein the compound is administered to the patient once daily.

5. The method of claim 4, wherein the compound is administered to the patient in the form of a pharmaceutically acceptable salt thereof.

6. The method of claim 5, wherein the pharmaceutically acceptable salt is 3-[2-fluoro-5-(2,3-difluoro-6methoxybenzyloxy)-4-methoxyphenyl]-2,4-dioxo-1,2,3,4-tetrahydrothieno[3,4-d]pyrimidine-5carboxylic acid choline salt.

7. The method of claim 1, wherein the compound is orally administered to the patient.

8. The method of claim 7, wherein the compound is administered to the patient in the form of a pharmaceutically acceptable salt thereof.

9. The method of claim 8, wherein the pharmaceutically acceptable salt is 3-[2-fluoro-5-(2,3-difluoro-6methoxybenzyloxy)-4-methoxyphenyl]-2,4-dioxo-1,2,3,4-tetrahydrothieno[3,4-d]pyrimidine-5carboxylic acid choline salt.

10. The method of claim 9, wherein the compound is administered to the patient once daily.

11. A method of reducing estrogen secretion in a human patient having endometriosis, the method comprising administering to the patient a compound represented by 3-[2-fluoro-5-(2,3-difluoro-6-methoxybenzyloxy)-4methoxyphenyl]-2,4-dioxo-1,2,3,4-tetrahydrothieno[3,4-d]pyrimidine-5-carboxylic acid, or a pharmaceutically acceptable salt thereof, wherein the compound is administered to the patient in an amount of 75 mg, calculated as a free form, per day.

12. The method of claim 11, wherein the compound is administered to the patient in the form of a pharmaceutically acceptable salt thereof.

13. The method of claim 12, wherein the pharmaceutically acceptable salt is 3-[2-fluoro-5-(2,3-difluoro-6methoxybenzyloxy)-4-methoxyphenyl]-2,4-dioxo-1,2,3,4-tetrahydrothieno[3,4-d]pyrimidine-5carboxylic acid choline salt.

14. The method of claim 11, wherein the compound is administered to the patient once daily.

15. The method of claim 14, wherein the compound is administered to the patient in the form of a pharmaceutically acceptable salt thereof.

16. The method of claim 15, wherein the pharmaceutically acceptable salt is 3-[2-fluoro-5-(2,3-difluoro-6methoxybenzyloxy)-4-methoxyphenyl]-2,4-dioxo-1,2,3,4-tetrahydrothieno[3,4-d]pyrimidine-5carboxylic acid choline salt.

17. The method of claim 11, wherein the compound is orally administered to the patient.

18. The method of claim 17, wherein the compound is administered to the patient in the form of a pharmaceutically acceptable salt thereof.

19. The method of claim 18, wherein the pharmaceutically acceptable salt is 3-[2-fluoro-5-(2,3-difluoro-6methoxybenzyloxy)-4-methoxyphenyl]-2,4-dioxo-1,2,3,4-tetrahydrothieno[3,4-d]pyrimidine-5carboxylic acid choline salt.

20. The method of claim 19, wherein the compound is administered to the patient once daily.

* * * * *